(12) United States Patent
Saido et al.

(10) Patent No.: US 7,572,574 B2
(45) Date of Patent: Aug. 11, 2009

(54) METHOD OF MEASURING NEPRILYSIN ACTIVITY

(75) Inventors: Takaomi Saido, Saitama (JP); Nobuhisa Iwata, Saitama (JP); Satoshi Tsubuki, Saitama (JP); Yoshie Takaki, Saitama (JP); Takashi Saito, Saitama (JP); Tadashi Nakaya, Hokkaido (JP)

(73) Assignees: Riken, Saitama (JP); Takeda Pharmaceutical Company, Ltd, Osaka (JP)

( * ) Notice: Subject to any disclaimer, the term of this patent is extended or adjusted under 35 U.S.C. 154(b) by 0 days.

(21) Appl. No.: 10/512,588

(22) PCT Filed: Apr. 24, 2003

(86) PCT No.: PCT/JP03/05239

§ 371 (c)(1),
(2), (4) Date: Jul. 15, 2005

(87) PCT Pub. No.: WO03/091449

PCT Pub. Date: Nov. 6, 2003

(65) Prior Publication Data

US 2006/0008842 A1    Jan. 12, 2006

(30) Foreign Application Priority Data

Apr. 26, 2002    (JP)    ............... 2002-126257
Sep. 6, 2002    (JP)    ............... 2002-261250

(51) Int. Cl.
*C12Q 1/00*    (2006.01)
*G01N 33/53*    (2006.01)
*G01N 33/567*    (2006.01)
*G01N 33/542*    (2006.01)
*G01N 33/537*    (2006.01)

(52) U.S. Cl. ............... 435/4; 435/7.1; 435/7.21; 435/7.8; 435/7.9; 435/7.92; 436/501

(58) Field of Classification Search ............... None
See application file for complete search history.

(56) References Cited

FOREIGN PATENT DOCUMENTS

EP    0 469 766 A1    7/1991
JP    10-174587    6/1998
WO    WO 90/10715    9/1990

OTHER PUBLICATIONS

Hama et al. J. Biochem, 2001, 130, pp. 721-726.*
Haruhiko Akiyama et al., 2001, Brain Research, 902, pp. 277-281.*

Back et al., "Histochemical Visualization of Neutral Endopeptidase-24.11 (Enkephalinase) Activity in Rat Brain: Cellular Localization and Codistribution with Enkephalins in the Globus Pallidus," The Journal of Neuroscience 9(12):4439-4455 (1989).
Waters et al., "Alterations of Substance P Metabolism and Neuropeptidases in Alzheimer's Disease," Journal of Gerontology 50A(5):B315-B319 (1995).
Jeohn et al., "Purification and Characterization of a Vasoactive Intestinal Polypeptide-degrading Endoprotease from Porcine Antral Mucosal Membranes," The Journal of Biological Chemistry 270(14):7809-7815 (1995).
Feindt et al., "Meningeal cells are targets and inactivation sites for the neuropeptide somatostatin," Molecular Brain Research 44:293-300 (1997).
Weber et al., "Metabolic Half-life of Somatostatin and Peptidase Activities Are Altered in Alzheimer's Disease," Journal of Gerontology 47(1):B18-B25 (1992).
Gourlet et al. "Vasoactive Intestinal Peptide (VIP) and Pituitary Adenylate Cyclase-Activating Peptide (PACAP-27, but not PACAP-38) Degradation by the Neutral Endopeptidase EC 3.4.24.11," Biochemical Pharmacology 54:509-515 (1997).
Shirotani et al., "Neprilsyn Degrades Both Amyloid B Peptides 1-40 and 1-42 Most Rapidly and Efficiently among Thiorphan-and Phosphoramidon-sensitive Endopeptidases," The Journal of Biologial Chemistry 276:21895-21901 (2001).
Iwata et al., "Metabolic Regulation of Brian Aβ by Neprilysin," Science 292:1550-1552, 2001.
Iwata et al., "Identification of the Major $A\beta_{1-42}$-degrading Catabolic Pathway in Brain Parenchyma: Suppression Leads to Biochemical and Pathological Deposition," Nature Medicine 6:143-150, 2000.
Yosojima et al., "Reduced Neprilysin in High Plague Areas of Alzeimer Brain: a Possible Relationship to Deficient Degradation of Beta-Amyloid Peptide." Neuroscience Letters 297: 97-100, 2001.

* cited by examiner

*Primary Examiner*—Olga N Chernyshev
(74) *Attorney, Agent, or Firm*—Edwards Angell Palmer & Dodge LLP; David G. Conlin; Melissa Hunter-Ensor, Esq.

(57)    ABSTRACT

The present invention provides a method of measuring the activity of neprilysin, etc. More specifically, the present invention provides a method of measuring the activity of neprilysin in nerve cells; a method of screening a protein, a peptide or a compound enhancing the activity or expression of neprilysin nerve cells by measuring the activity of neprilysin; a method of enhancing the activity or expression of neprilysin; and so on. Thus, the compound enhancing the activity and/or expression of neprilysin, which is obtained by the screening method characterized by using the method of measuring the activity of neprilysin in accordance with the present invention, is useful as a preventive and/or therapeutic agent for Alzheimer's disease. The method of measuring the activity of the present invention can be used for presymptoms diagnosis of Alzheimer's disease.

18 Claims, 4 Drawing Sheets

METHOD OF MEASURING NEPRILYSIN ACTIVITY

CROSS-REFERENCE TO RELATED APPLICATION(S)

This application is a §371 application of copending international patent application PCT/JP03/05239 which was filed on Apr. 24, 2003, which is incorporated by reference.

TECHNICAL FIELD

The present invention relates to a method of promoting the degradation of amyloid β protein (Aβ) deeply associated with the onset/progression of Alzheimer's disease to reduce Aβ levels in the brain and improve the symptoms of Alzheimer's disease. That is, the present invention relates to a method of enhancing the activity or expression of neprilysin, which is an enzyme responsible for the degradation of Aβ in the brain; a method of measuring the activity of neprilysin in nerve cells; and a method of screening a protein, a peptide or a compound enhancing the activity or expression of neprilysin in nerve cells by measuring the activity of neprilysin. The present invention further relates to a pharmaceutical composition comprising the protein, peptide or compound controlling the degradation of Aβ, which is found by the screening method; a method of treating disease and a method of preventing disease.

BACKGROUND ART

Alzheimer's disease is a neurodegenerative disorder of which the main symptom is dementia. In Alzheimer's disease patients, atrophy of the cerebral cortex is found and pathologically, the characteristic lesions including senile plaques, changes in neurofibrillary tangles, etc. are observed, in addition to severe loss of nerve cells. Among them, the pathological change observed from a relatively early stage is the formation of senile plaques and since a major component in the senile plaques is amyloid β protein (Aβ), it is considered that abnormalities in the formation or degradation of AD would be closely associated with the onset/progression of Alzheimer's disease. Aβ is cleaved with and produced from the Aβ precursor protein (βAPP) by β-secretase (Science, 286, 735-741, 1999) and γ-secretase, which belong to aspartic proteases. With regard to γ-secretase, it has been revealed that a familial Alzheimer's disease (FAD)-pathogenic gene, presenilin or a presenilin-containing complex takes part in expressing the activity (Nature, 398, 513-517, 1999; Nature, 405, 689-694, 2000).

This Aβ is steadily synthesized/secreted in vivo and it is considered that under normal conditions Aβ will be rapidly degraded but not accumulated. When this degradability decreases for some reason, it results in accumulation of Aβ and conversely when the degradability is enhanced, the accumulation of Aβ can be prevented. Recently, it was clarified that the major enzyme involved in the degradation of Aβ is a neutral endopeptidase, neprilysin (Nature Med., 6, 143-151, 2000). In neprilysin knockout mice, the Aβ level elevated in the brain and the elevation was most remarkable in the hippocampus (Science, 292, 1550-1552, 2001). It was further clarified that the expression of neprilysin declined in the brain of Alzheimer's disease patients (Neuroscience Lett., 297, 97-100, 2001).

It is considered that when the activity or expression of neprilysin enhances to increase degradability of Aβ, clearance of Aβ in the brain will increase to downregulate the accumulation of Aβ. However, the mechanism concerning the downregulation of neprilysin expression is not very clear. Neprilysin is a neutral endopeptidase and has an action of degrading various peptides in the brain. Since a number of physiologically active peptides are present in the brain, there is a possibility that a peptide regulating the expression of neprilysin mediated by GPCR (G-protein coupled receptor) as a receptor or by a nuclear receptor would be present among them. Once the peptide in the brain which regulates the expression of neprilysin can be found, a method of searching a novel drug promoting Aβ degradation can be provided and furthermore, application to novel pharmaceuticals such as therapeutic or preventive agents for Alzheimer's disease, etc. can be provided.

DISCLOSURE OF THE INVENTION

In order to explore a brain peptide regulating the activity of neprilysin in nerve cells, the present inventor found a method of visualizing the activity of neprilysin in mouse primary nerve cells using a fluorescent substrate. Using this measuring system, various brain peptides were acted on to explore a peptide affecting the activity of neprilysin. As a result, the inventor has found that somatostatin enhances the activity of neprilysin in primary nerve cells and has come to accomplish the present invention.

That is, the present invention provides the following features.

(1) In a method of measuring the activity of neprilysin using a fluorescent substance, the method of measuring the activity of neprilysin which comprises using an isolated nerve cell or an immobilized nerve cell;

(2) The method of measuring the activity of neprilysin according to (1), wherein an isolated and immobilized nerve cell is used;

(3) The method of measuring the activity of neprilysin according to (1), wherein a nerve cell immobilized with paraformaldehyde is used;

(4) The measuring method according to (1), wherein the nerve cell is a cultured cell;

(5) The measuring method according to (4), wherein the cultured cell is a primary cultured cell;

(6) The measuring method according to (1), wherein dendrites of the nerve cell are used;

(7) The measuring method according to (1), wherein an axon of the nerve cell is used;

(8) The measuring method according to (1), wherein the synaptic terminal of the nerve cell is used;

(9) The measuring method according to (1), wherein synaptic vesicles of the nerve cell are used;

(10) The measuring method according to (1), wherein the nerve cell prepared from the cerebral cortex or the hippocampus is used;

(11) The measuring method according to (1), wherein the fluorescent substance is the reaction product of 4-methoxy-2-naphthylamide and nitrosalicylaldehyde;

(12) The measuring method according to (11), wherein 4-methoxy-2-naphthylamide is derived from a substrate of neprilysin;

(13) The measuring method according to (12), wherein the substrate of neprilysin is glutaryl-alanyl-alanyl-phenylalanyl-4-methoxy-2-naphthylamide;

(14) The measuring method according to (11), wherein 4-methoxy-2-naphthylamide is obtained by treating glutaryl-alanyl-alanyl-phenylalanyl-4-methoxy-2-naphthylamide with neprilysin and then with an aminopeptidase;

(15) The measuring method according to (1), wherein the fluorescent substance is 7-amino-4-methylcoumarine;
(16) The measuring method according to (15), wherein 7-amino-4-methylcoumarine is obtained by treating succinyl-alanyl-alanyl-phenylalanine 4-methylcoumarin-7-amide with neprilysin;
(17) A method of screening a compound or its salt enhancing the activity of neprilysin, which comprises using the measuring method according to (1);
(18) A compound or its salt enhancing the activity of neprilysin, which is obtainable using the screening method according to (17);
(19) A pharmaceutical comprising the compound or its salt according to (18);
(20) The pharmaceutical according to (19), which is a preventive and/or therapeutic agent, a symptom-improving agent or a progression-retarding agent for Alzheimer's disease;
(21) A method of screening a compound or its salt enhancing the expression of neprilysin, which comprises using the measuring method according to (1);
(22) A compound or its salt enhancing the activity of neprilysin, which is obtainable using the screening method according to (21);
(23) A pharmaceutical comprising the compound or its salt according to (22);
(24) The pharmaceutical according to (23), which is a preventive and/or therapeutic agent, a symptom-improving agent or a progression-retarding agent for Alzheimer's disease;
(25) A method of diagnosis for Alzheimer's disease, which comprises using the method of measuring the activity according to (1);
(26) An agent for enhancing the activity of neprilysin comprising somatostatin, a protein containing substantially the same amino acid sequence as somatostatin or its partial peptide, an agonist of somatostatin receptor or a salt thereof;
(27) An agent for enhancing the expression of neprilysin comprising somatostatin, a protein containing substantially the same amino acid sequence as somatostatin or its partial peptide, an agonist of somatostatin receptor or a salt thereof;
(28) A method of enhancing the activity of neprilysin, which comprises administering to a mammal an effective dose of somatostatin, a protein containing substantially the same amino acid sequence as somatostatin or its partial peptide, an agonist of somatostatin receptor or a salt thereof;
(29) A method of enhancing the expression of neprilysin, which comprises administering to a mammal an effective dose of somatostatin, a protein containing substantially the same amino acid sequence as somatostatin or its partial peptide, an agonist of somatostatin receptor or a salt thereof;
(30) A method of enhancing the activity or expression of neprilysin, which comprises promoting the activity of somatostatin receptor in a mammal;
(31) Use of somatostatin, a protein containing substantially the same amino acid sequence as somatostatin or its partial peptide, an agonist of somatostatin receptor or a salt thereof to manufacture an agent for enhancing the activity or expression of neprilysin;
(32) An agent for enhancing the activity of neprilysin comprising substance P, a protein containing substantially the same amino acid sequence as substance P or its partial peptide, an agonist of substance P receptor or a salt thereof;
(33) An agent for enhancing the expression of neprilysin comprising substance P, a protein containing substantially the same amino acid sequence as substance P or its partial peptide, an agonist of substance P receptor or a salt thereof;
(34) A method of enhancing the activity of neprilysin, which comprises administering to a mammal an effective dose of substance P, a protein containing substantially the same amino acid sequence as substance P or its partial peptide, an agonist of substance P receptor or a salt thereof;
(35) A method of enhancing the expression of neprilysin, which comprises administering to a mammal an effective dose of substance P, a protein containing substantially the same amino acid sequence as substance P or its partial peptide, an agonist of substance P receptor or a salt thereof;
(36) A method of enhancing the activity or expression of neprilysin, which comprises promoting the activity of substance P receptor in a mammal;
(37) Use of substance P, a protein containing substantially the same amino acid sequence as substance P or its partial peptide, an agonist of substance P receptor or a salt thereof to manufacture an agent for enhancing the activity or expression of neprilysin;
(38) An agent for enhancing the activity of neprilysin comprising an antagonist of pituitary adenylate cyclase-activating polypeptide receptor, or a salt thereof;
(39) An agent for enhancing the expression of neprilysin comprising an antagonist of pituitary adenylate cyclase-activating polypeptide receptor, or a salt thereof;
(40) A method of enhancing the activity of neprilysin, which comprises administering an effective dose of an antagonist of pituitary adenylate cyclase-activating polypeptide receptor, or a salt thereof, to a mammal;
(41) A method of enhancing the expression of neprilysin, which comprises administering an effective dose of an antagonist of pituitary adenylate cyclase-activating polypeptide receptor, or a salt thereof, to a mammal;
(42) A method of enhancing the activity or expression of neprilysin, which comprises inhibiting the activity of pituitary adenylate cyclase-activating polypeptide receptor in a mammal;
(43) Use of an antagonist of pituitary adenylate cyclase-activating polypeptide receptor or a salt thereof to manufacture an agent for enhancing the activity or expression of neprilysin;
(44) An agent for enhancing the activity of neprilysin comprising an antagonist of vasoactive intestinal peptide receptor or a salt thereof;
(45) An agent for enhancing the expression of neprilysin comprising an antagonist of vasoactive intestinal peptide receptor or a salt thereof;
(46) A method of enhancing the activity of neprilysin, which comprises administering an effective dose of vasoactive intestinal peptide receptor or a salt thereof to a mammal;
(47) A method of enhancing the expression of neprilysin, which comprises administering an effective dose of vasoactive intestinal peptide receptor or a salt thereof to a mammal;
(48) A method of enhancing the activity or expression of neprilysin, which comprises inhibiting the activity of vasoactive intestinal peptide receptor in a mammal;
(49) Use of an antagonist of vasoactive intestinal peptide receptor or a salt thereof to manufacture an agent for enhancing the activity or expression of neprilysin; and the like.

The present invention further provides:
(50) a method of preventing and/or treating Alzheimer's disease, which comprises enhancing the activity or expression of neprilysin.

Hereinafter the present invention is described in detail.

BEST MODE FOR CARRYING OUT THE INVENTION (1) Method of Measuring the Activity of Neprilysin In a first embodiment of the present invention, it is provided a method of measuring the activity of neprilysin using a fluorescent substance, characterized by using an isolated nerve cell (viable cell) or a fixed nerve cell (preferably, an isolated and fixed nerve cell).

The nerve cell used in the measuring method of the present invention is normally collected from any of brain regions (e.g., olfactory bulb, amygdaloid nucleus, basal ganglia, hippocampus, thalamus, hypothalamus, subthalamic nucleus, cerebral cortex, medulla oblongata, cerebellum, occipital lobes, frontal lobe, lateral lobe, putamen, caudate nucleus, corpus callosum, substantia nigra), using publicly known methods (methods described in, e.g., Culturing Nerve Cells (The MIT press, 1991), etc.). Preferably, the nerve cell collected from the cerebral cortex or hippocampus is used in the present invention.

In the present invention, the nerve cell collected/isolated as described above can be used as it is, but usually, the collected cell is cultured and the resulting cultured cell is used. Since the property of cell becomes stable and sticky by culturing the cell, a primary cultured cell is preferably used. Further in view of the function of nerve cells, it is preferred to use the dendrites, axons, synaptic terminals, synaptic vesicles, etc. of nerve cells, not the whole nerve cell.

Culture is performed under conditions appropriately selected by one skilled in the art. For example, the cells collected from the regions as described above are cultured on a microtiter plate or a chamber slide in a medium such as serum-supplemented Neurobasal Medium (LifeTech), serum-supplemented DEME, serum-supplemented MEM, etc. at 37° C. in the presence of 5% $CO_2$ for 4 to 6 days.

Alternatively, culture may be performed for about 21 to about 28 days. As will be later described, the cells are ordinarily observed microscopically in the measuring method of the present invention and, it is advantageous to culture the nerve cells obtained on a chamber slide.

In the measuring method of the present invention, a test compound, etc. are added to the cells and after incubation for a given period of time, the cells are preferably fixed using a fixing agent. As the cell fixing agent used in the present invention, there are paraformaldehyde, formalin, acetone, etc. The cell fixing agent advantageously used in the present invention is paraformaldehyde. Conditions for the fixation can be appropriately selected by one skilled in the art (see the literature such as Current Protocols in Cell Biology (John Wiley & Sons, NIH), etc.). The fixation is effected by treating the cells, e.g., in a paraformaldehyde solution (1.5% paraformaldehyde/50 mM phosphate buffer, pH 6.8) for 10 to 40 minutes.

In one embodiment of the measuring method of the present invention, a test compound and a substrate solution are reacted with the isolated/fixed cells as described above, followed by further adding a solution mixture of aminopeptidase and phosphoramidone and a nitrosalicylaldehyde solution to the mixture and reacting them. Examples of the substrate used here are synthetic substrates such as glutaryl-alanyl-alanyl-phenylalanyl-4-methoxy-2-naphthylamide, glutaryl-alanyl-alanyl-phenylalanyl-2-napthylamide, succinyl-alanyl-alanyl-phenylalanine 4-methylcoumarin-7-amide, etc. A preferred substrate is glutaryl-alanyl-alanyl-phenylalanyl-4-methoxy-2-naphthylamide. Reaction conditions for the reactions described above may be suitably chosen by one skilled in the art, depending upon cells used, substrate, kind/amount of test compound, etc. For example, where the nerve cell prepared from the cerebral cortex, hippocampus, etc. is used as the cell and glutaryl-alanyl-alanyl-phenylalanyl-4-methoxy-2-naphthylamide is used as the substrate, the reaction of the cell with a test compound and a substrate solution is carried out at 0 to 20° C. for 1 to 72 hours. The following reaction with the solution mixture of aminopeptidase and phosphoramidone and a nitrosalicylaldehyde solution is carried out, e.g., at 20 to 40° C. for 10 to 60 minutes.

In the reactions described above, a compound used as the substrate is degraded by the neprilysin and aminopeptidase treatment and the product obtained by the degradation is reacted with, e.g., nitrosalicylaldehyde to form a fluorescent substance. When glutaryl-alanyl-alanyl-phenylalanyl-4-methoxy-2-naphthylamide is used as the substrate, this is degraded to form free 4-methoxy-2-naphthylamine (MNA). This free MNA is reacted with nitrosalicylaldehyde to form an insoluble yellow fluorescent substance. On the other hand, when succinyl-alanyl-alanyl-phenylalanine 4-methylcoumarin-7-amide is used as the substrate, the amide is degraded to form 7-amino-4-methylcoumarine.

In the measuring method of the present invention, the reactions as described above are carried out and positive stained images by the produced fluorescent substance are observed, e.g., under a confocal laser scanning microscope with an Argon laser and a filter for rhodamine.

The enhanced neprilysin activity or gene expression can be quantified from the stained images obtained in the activity measurement described above by digitalizing its fluorescence intensity, using software for image analysis. As the software, there are used MetaVue from Nippon Roper Co., Ltd., and the like.

(2) Method of Screening a Compound Enhancing the Activity and/or Expression of Neprilysin Using Neprilysin Activity Staining In another embodiment of the present invention, there is provided a method of screening a compound or its salt enhancing the activity of neprilysin, which comprises using the method of measuring the activity of neprilysin described above. That is, a compound (e.g., a peptide, a protein, a non-peptide compound, a synthetic compound, a fermentation product, etc.) enhancing the activity and/or expression of neprilysin, or a salt thereof can be efficiently screened using the neprilysin activity staining of the present invention.

Such a compound includes (a) a compound having the effect of promoting (or enhancing) the neprilysin activity, (b) a compound having the effect of increasing (or enhancing) the expression of neprilysin gene, and the like.

Specifically, in the screening method of the present invention, a compound enhancing the activity or expression of neprilysin, or a salt thereof, is screened by the method, which comprises comparing (i) the case that a nerve cell alone is used without using a test compound and (ii) the case that the nerve cell is treated with the test compound, in terms of the neprilysin activity (e.g., the activity determined from neprilysin inhibition induced by thiorphan, which is a specific enzyme inhibitor of neprilysin; etc.).

More specifically, the nerve cell prepared as described above is first incubated on a chamber slide. After incubation of the cell, a test compound is added to the cell in an amount sufficiently reacting with the cell, though the amount depends on kind or concentration of the test compound. After incubation for a given period of time (e.g., for 24 hours in a final concentration of 1 µM in the case of somatostatin later described), the cell is fixed with paraformaldehyde. The fixed cell is reacted with a substrate solution (glutaryl-alanyl-alanyl-phenylalanyl-4-methoxy-2-naphthylamide) and an aminopeptidase-phosphoramidone solution mixture and a nitrosalicylaldehyde solution is further added to and reacted with the reaction mixture. Reaction conditions for these reactions are the same as described above. After the reaction, positive stained images are observed under a confocal laser scanning microscope using an Argon laser and a filter for rhodamine.

In the screening method of the present invention, for example, peptides (for example, angiotensin, bombesin, canavinoid, cholecystokinin, glutamine, serotonin, melatonin, neuropeptide Y, opioids, purines, vasopressin, oxytocin, substance P, PACAP, secretin, glucagon, calcitonin, adrenomedulin, somatostatin, GHRH, CRF, ACTH, GRP, PTH, VIP, dopamine, motilin, amylin, bradykinin, CGRP (calcitonin gene-related peptide), pancreastatin, thromboxane, adrenaline, the chemokine superfamily, endothelin, enterogastrin, histamine, neurotensin, TRH, pancreatic polypeptide, galanin), proteins, non-peptide compounds, synthetic compounds, fermentation products, cell extracts, vegetable extracts, animal tissue extracts, etc. are employed as the test compound. These compounds may be novel compounds or publicly known compounds. Also, at least two of these compounds may be mixed and the mixture may be provided as a sample. Preferred test compounds in the screening method of the present invention are a protein containing substantially the same amino acid sequence as somatostatin or its partial peptide, an agonist of somatostatin receptor or its salt, a protein containing substantially the same amino acid sequence as substance P or its partial peptide, an agonist of substance P receptor or its salt and, PACAP and VIP receptor antagonists or salts thereof, which will be later described.

In the screening method, when the nerve cell is treated with a test compound and the neprilysin activity increases by about 10% or more, preferably by about 30% or more and more preferably by about 50% or more, the test compound can be selected as a compound having the effect of enhancing the activity or expression of neprilysin.

(3) Pharmaceutical Comprising the Compound obtained as a Result of Screening

The compound obtained using the screening method is a compound selected from the test compounds described above and has the effect of enhancing the activity or expression of neprilysin. Thus, the compound can be used as a pharmaceutical, such as a safe and low toxic preventive and/or therapeutic agent for Alzheimer's disease, etc. In addition, compounds derived from the compound obtained by the screening described above can be used as well.

(4) Method for Diagnosis of Alzheimer's Disease

By using the activity measuring method of the present invention, presymptomatic diagnosis of Alzheimer's disease can be made. That is, the results obtained by the activity measurement of the present invention are quantified and the quantified values are compared with those obtained with control. It is thus possible to predict a risk of developing Alzheimer's disease in its subject.

(5) Agent for Enhancing the Neprilysin Activity

In a still other embodiment of the present invention, there is provided the agent for enhancing the activity of neprilysin or the agent for enhancing the expression of neprilysin comprising somatostatin, a protein containing substantially the same amino acid sequence as somatostatin or its partial peptide, or an agonist of somatostatin receptor or its salt. Somatostatin is a publicly known protein (peptide) composed of 14 amino acids (Ala-Gly-Cys-Lys-Asn-Phe-Phe-Trp-Lys-Thr-Phe-Thr-Ser-Cys; SEQ ID NO: 1) and is disclosed in, e.g., Proc. Natl. Acadi. Sci. USA, 80, 6932-6936, 1983; Science, 224, 168-171, 1984, etc.

Herein, "substantially the same amino acid sequence" is used to mean an amino acid sequence having at least about 50% homology, preferably at least about 60% homology, more preferably at least about 70% homology, much more preferably at least about 80% homology, particularly preferably at least about 90% homology and most preferably at least about 95% homology, to the amino acid sequence to be compared. Also, the "partial peptide" may be any peptide so far as it is a partial peptide of somatostatin but preferably include a peptide having the sequence of at least 3, preferably at least 5, and more preferably at least 7 amino acids, in the constituent amino acid sequence, and the like.

By administering to a mammal an effective dose of somatostatin, a protein containing substantially the same amino acid sequence as somatostatin or its partial peptide, an agonist of somatostatin receptor or its salt, the activity of neprilysin or the expression of neprilysin in the target mammal can be enhanced.

In a still other embodiment of the present invention, there is provided the agent for enhancing the activity of neprilysin or the agent for enhancing the expression of neprilysin comprising substance P, a protein containing substantially the same amino acid sequence as substance P or its partial peptide, or an agonist of substance P receptor or its salt. Substance P is a publicly known peptide composed of 11 amino acids (Arg-Pro-Lys-Pro-Gln-Gln-Phe-Phe-Gly-Leu-Met; SEQ ID NO: 2) and is disclosed in, e.g., Neuropeptides: Regulators of Physiological Processes, (Fleur L. Strand, ed.), The MIT Press, Massachusetts, 1999, etc.

Herein, "substantially the same amino acid sequence" is used to mean an amino acid sequence having at least about 50% homology, preferably at least about 60% homology, more preferably at least about 70% homology, much more preferably at least about 80% homology, particularly preferably at least about 90% homology and most preferably at least about 95% homology, to the amino acid sequence to be compared. Also, the "partial peptide" may be any peptide so far as it is a partial peptide of substance P but preferably include a peptide having the sequence of at least 3, preferably at least 5, and more preferably at least 7 amino acids, in the constituent amino acid sequence, and the like.

By administering to a mammal an effective dose of substance P, a protein containing substantially the same amino acid sequence as substance P or its partial peptide, an agonist of substance P receptor or its salt, the activity of neprilysin or the expression of neprilysin in the target mammal can be enhanced.

In a still other embodiment of the present invention, there is provided the agent for enhancing the activity of neprilysin or the agent for enhancing the expression of neprilysin comprising the antagonist of PACAP receptor, VIP receptor, etc., or a salt thereof. These are publicly known peptides disclosed in Neuropeptides: Regulators of Physiological Processes, (Fleur L. Strand, ed.), The MIT Press, Massachusetts, 1999, etc.

PACAP or VIP inhibitorily acts against the neprilysin activity or its gene expression. Therefore, by administering to a mammal an effective dose of antagonist of PACAP receptor, VIP receptor, etc., or a salt thereof, the activity of neprilysin or the expression of neprilysin can be enhanced in the target mammal.

In the present invention, a novel agent for enhancing the activity or expression of neprilysin can be screened using the known agents for enhancing the activity or expression of neprilysin described above as probes. That is, a novel agent for enhancing the activity or expression of neprilysin can be screened by comparing the level of the activity or expression of neprilysin when a test compound is added to neprilysin, with the level of the neprilysin activity or expression when no test compound is added to neprilysin, the activity or expression of neprilysin being enhanced by somatostatin, the agonist of somatostatin receptor, substance P, the agonist of substance P receptor, the agonists to PACAP and VIP receptors, or the like. Alternatively, a novel agent for enhancing the activity or expression of neprilysin can be screened by comparing the level of the activity or expression of neprilysin enhanced by somatostatin, the agonist of somatostatin receptor, substance P, the agonist of substance P receptor, the agonists to PACAP and VIP receptors, or the like, with the level of the activity or expression of neprilysin enhanced by a test compound. As the test compound, there are used, for example, peptides (e.g., angiotensin, bombesin, canavinoid, cholecystokinin, glutamine, serotonin, melatonin, neuropeptide Y, opioids, purines, vasopressin, oxytocin, substance P, PACAP, secretin, glucagon, calcitonin, adrenomedulin, somatostatin, GHRH, CRF, ACTH, GRP, PTH, VIP, dopamine, motilin, amylin, bradykinin, CGRP (calcitonin gene-related peptide), pancreastatin, thromboxane, adrenaline, the chemokine superfamily, endothelin, enterogastrin, histamine, neurotensin, TRH, pancreatic polypeptide, galanin), proteins, non-peptide compounds, synthetic compounds, fermentation products, cell extracts, vegetable extracts, animal tissue extracts, etc. are employed as the test compound. These compounds may be novel compounds or publicly known compounds. Also, at least two of these compounds may be mixed and the mixture may be provided as a sample.

(6) Pharmaceutical Preparations, Dose, Administration Method, etc.

When it is intended to use the compounds obtained by the screening method using the activity measuring method of the present invention as agents for promoting Aβ degradation or removing Aβ and furthermore as preventive and/or therapeutic agents for Alzheimer's disease, utilizing the neprilysin activity, the compounds can be prepared into pharmaceutical preparations in conventional manners.

Where the compounds described above can form pharmaceutically acceptable salts thereof, such salts may be formed. As these salts, there may be used salts with physiologically acceptable acids (e.g., inorganic acids, organic acids, etc.) or bases (e.g., alkali metal salts, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compounds described above (including salts thereof) can be used orally in the form of tablets which, if necessary, may be coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the active compounds described above with publicly known carriers recognized to be physiologically acceptable, flavoring agents, excipients, vehicles, antiseptics, stabilizers, binders, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include binders such as gelatin, corn starch, tragacanth or gum arabic, excipients such as crystalline cellulose, swelling agents such as corn starch, gelatin, alginic acid, etc., lubricants such as magnesium stearate, sweetening agents such as sucrose, lactose or saccharin, flavoring agents such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, which can be used in combination with a dissolution aid such as benzyl benzoate, benzyl alcohol, etc.

Furthermore, the preventive and/or therapeutic agents described above may also be formulated with buffers (e.g., phosphate buffer, sodium acetate buffer), soothing agents (e.g., benzalkonium chloride, procaine hydrochloride, etc.), stabilizers (e.g., human serum albumin, polyethylene glycol, etc.), preservatives (e.g., benzyl alcohol, phenol, etc.), antioxidants, etc. The thus prepared liquid for injection is normally filled in an appropriate ampoule.

The dose of the compound obtained in the present invention varies depending on subject to be administered, conditions, route for administration, etc.; in oral administration, the dose for a patient (as 60 kg) is normally about 0.1 mg to about 100 mg, preferably about 1.0 to about 50 mg, and more preferably about 1.0 to about 20 mg per day. In parenteral administration, the single dose may vary depending on subject to be administered, conditions, route for administration, etc. but it is advantageous to administer the compound intravenously to a patient (as 60 kg) in a daily dose of about 0.01 to about 30 mg, preferably about 0.1 to about 20 mg, and more preferably about 0.1 to about 10 mg. For other animal species, the corresponding dose as converted per 60 kg can be administered.

The thus obtained pharmaceutical preparation can be administered to human or other mammals (e.g., mice, rats, rabbits, sheep, swine, bovine, cats, dogs, monkeys, etc.).

In the specification and drawings, where the codes of bases, amino acids, etc. are denoted in abbreviations, they are based on the abbreviations in accordance with the IUPAC-IUB Commission on Biochemical Nomenclature or by the common codes in the art. For amino acids that may have the optical isomer, L form is presented unless otherwise indicated.

EXAMPLES

Example 1

Neprilysin Activity Staining in Primary Cultured Nerve Cells

Figure 1:
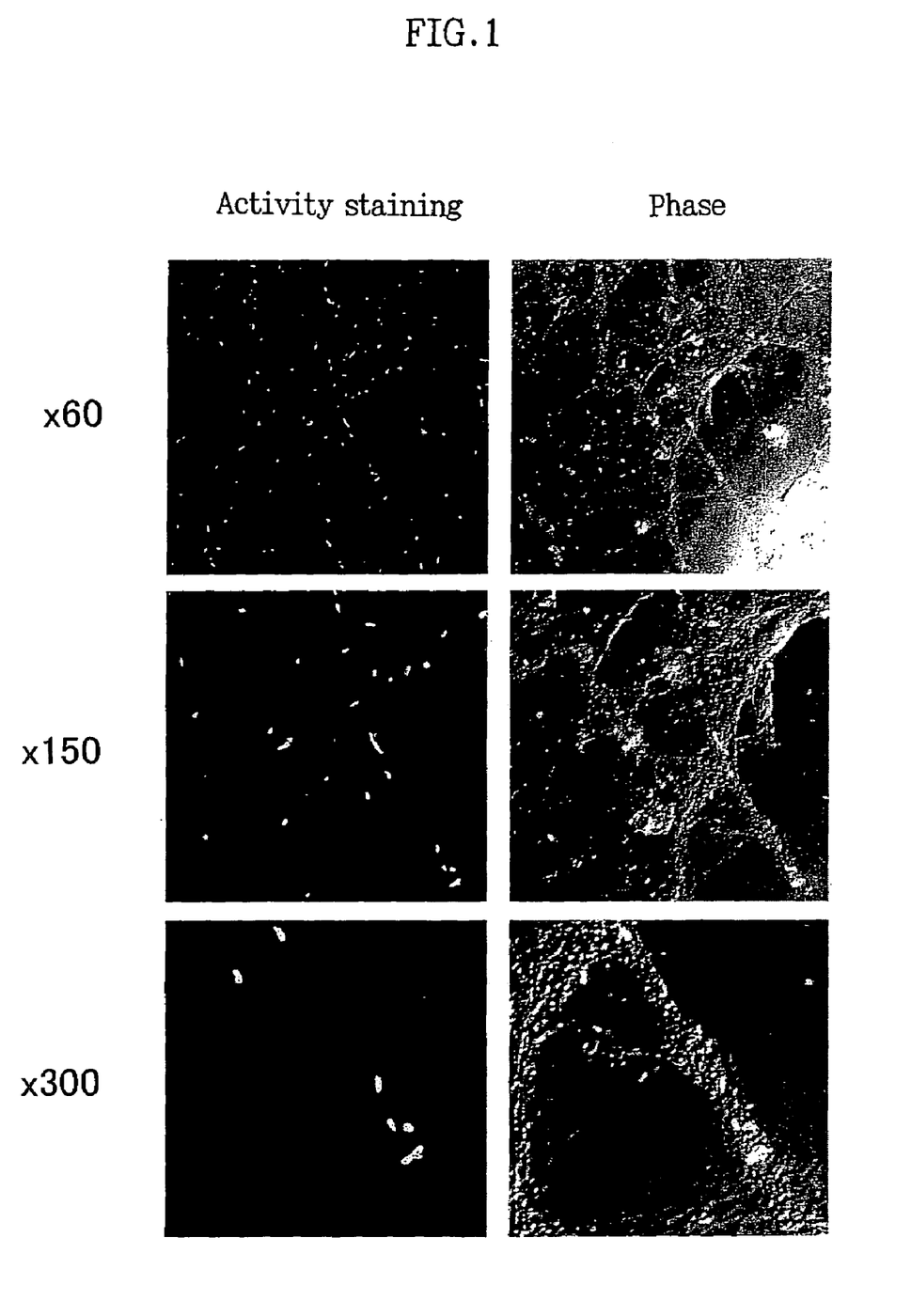
FIG. 1 is a microscopic photograph showing the results from the activity staining of the neprilysin activity in mouse primary cultured nerve cells.

Nerve cells were prepared from the mouse fetal cerebral cortex and hippocampus and seeded on a poly-L-coated chamber slide (8 chambers, IWAKI 4730-040) at a density of $1 \times 10^5$ cells/chamber, followed by incubation for 7 days. After completion of the incubation, the cells were washed with TBS (pH 7.4) and fixed for 12.5 minutes at 20° C. with a paraformaldehyde solution (1.5% paraformaldehyde/50 mM phosphate buffer, pH 6.8). After the cells were washed twice with TBS, 0.2 ml of substrate solution (glutaryl-alanyl-alanyl-phenylalanyl-4-methoxy-2-naphthylamide, Sigma G3769, fmal concentration: 0.5 mM; 0.05 M Tris-HCl buffer, pH 7.4 (pH was adjusted to 7.4 at 4° C.)) was added to the cells, followed by reacting at 4° C. for 48 hours. After completion of the reaction, 25 µl of the solution mixture of aminopeptidase (Sigma L-5006, final concentration: 20.4 µg/ml) and phosphoramidone (Peptide Inst. 4082, final concentration: 10 µM) and 25 µl of nitrosalicylaldehyde solution (6 mM) were further added thereto sequentially. The mixture was reacted at 37° C. for 30 minutes. The reaction was completed by washing the cells twice with TBS. Using argon laser and a filter for rhodamine, positive stained images were observed under a confocal laser scanning microscope (FIG. 1). When the substrate is degraded by neprilysin, an insoluble fluorescent reaction product is formed so that the sites where neprilysin is present are visualized in yellow. By this method it was confirmed that the enzyme activity of neprilysin was present in the primary cultured nerve cells of the mouse fetal cerebral cortex and hippocampus. The sites where neprilysin was present were prominent in the protruding parts of the nerve cells.

Example 2

Induction of the Neprilysin Enzyme Activity by Somatostatin

Figure 2:
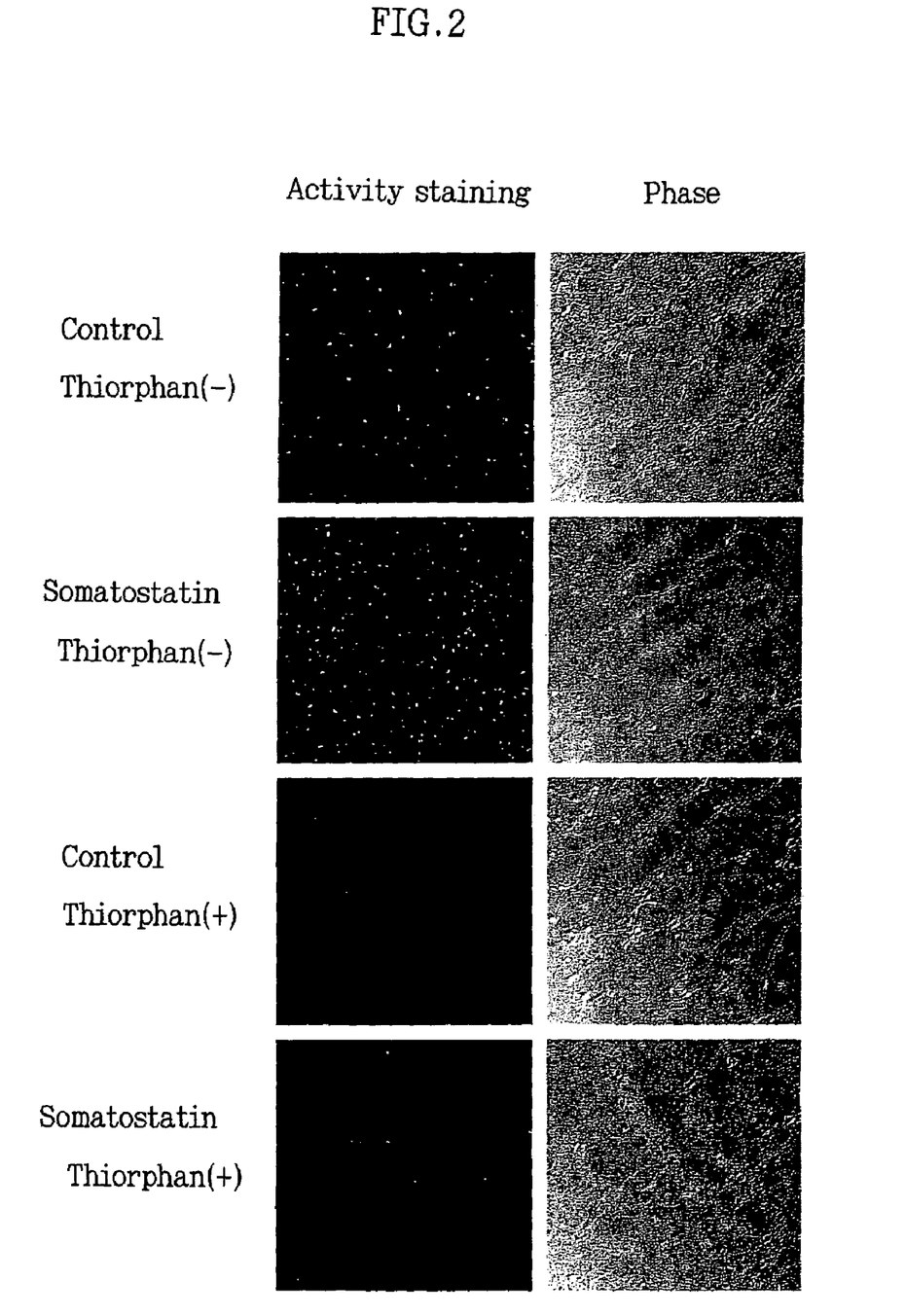
FIG. 2 is a microscopic photograph showing the effects of somatostatin and thiorphan against the neprilysin activity in mouse primary cultured nerve cells.
Figure 3:
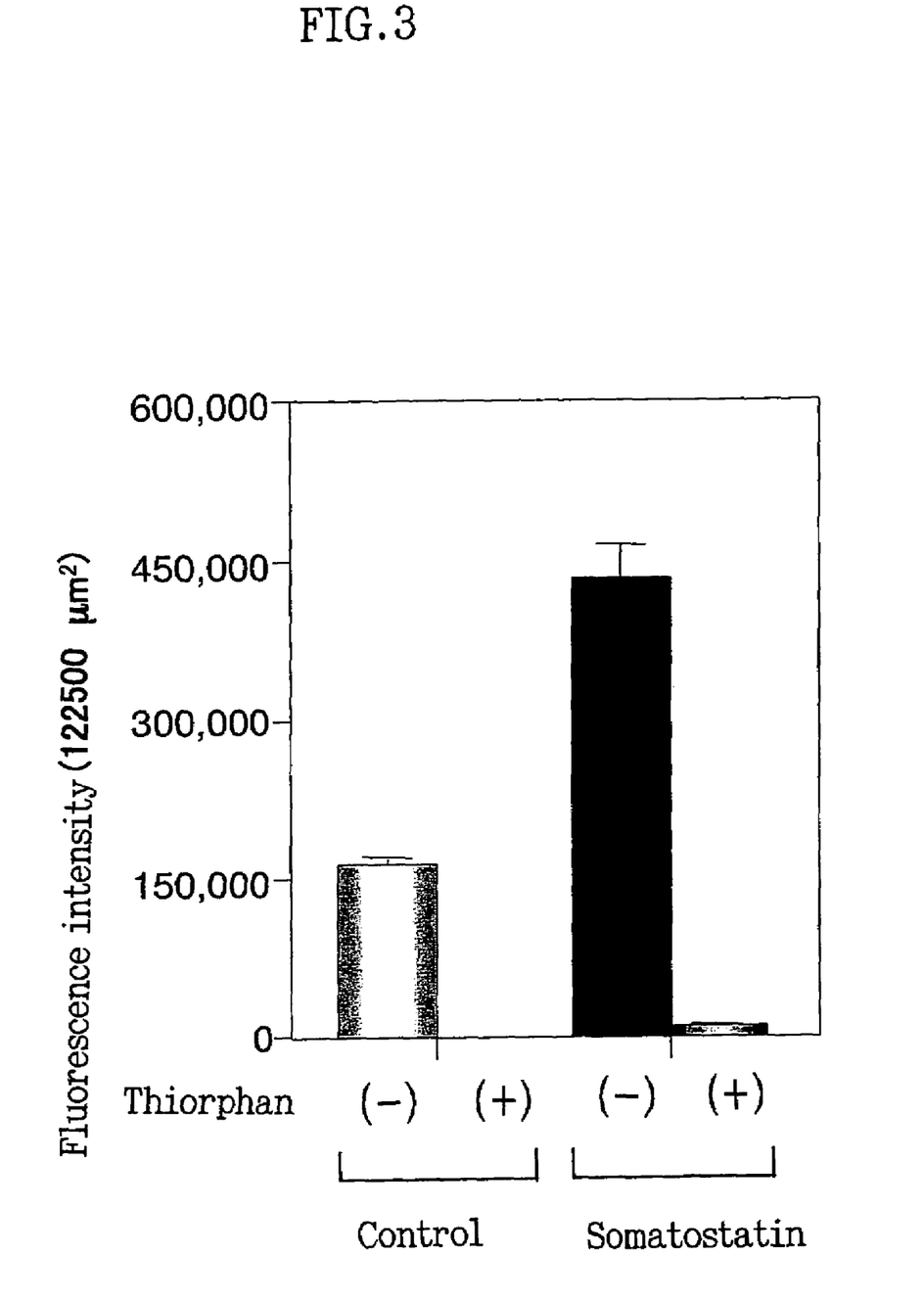
FIG. 3 shows the results of quantification of the stained images obtained in EXAMPLE 2 using image analysis software.

Nerve cells were prepared from the mouse fetal cerebral cortex and hippocampus, followed by incubation as in EXAMPLE 1. On day 7 of the incubation, somatostatin (somatostatin 14 and 28, final concentration: 1 µM) was added to the cells, followed by incubation for further 24 hours. After completion of the incubation, the neprilysin activity in the mouse primary cultured nerve cells was visualized and observed by the procedure shown in EXAMPLE 1 (FIG. 2). By the addition of somatostatin, the neprilysin activity in the nerve cells markedly increased as compared to control added with no somatostatin. It was confirmed that this neprilysin enzyme activity was specific to neprilysin, since the neprilysin enzyme activity almost completely disappeared by adding a neprilysin-specific enzyme inhibitor or thiorphan (Sigma -T6031, final concentration: 10 µM) to the substrate solution. To investigate in further detail, these stained images were quantified by image analysis software (Nippon Roper Co., Ltd., MetaVue) and examined. As a result, it was confirmed that the enzyme activity of neprilysin increased by about 2.5 times with somatostatin (FIG. 3).

Example 3

Regulation of the Neprilysin Enzyme Activity by Neuropeptides

Nerve cells were prepared from the mouse fetal cerebral cortex and hippocampus, followed by incubation as in EXAMPLE 1. On day 7 of the incubation, various neuropeptides such as substance P, PACAP, VIP, etc. (final concentration: 1 µM) was added to the cells, followed by incubation for further 24 hours. After completion of the incubation, the neprilysin activity in the mouse primary cultured nerve cells was visualized and observed by the procedure shown in EXAMPLE 1. The cells with markedly changed (enhanced or inhibited) neprilysin activity by the addition of the peptides as compared to control added with no peptide were selected.

Figure 4:
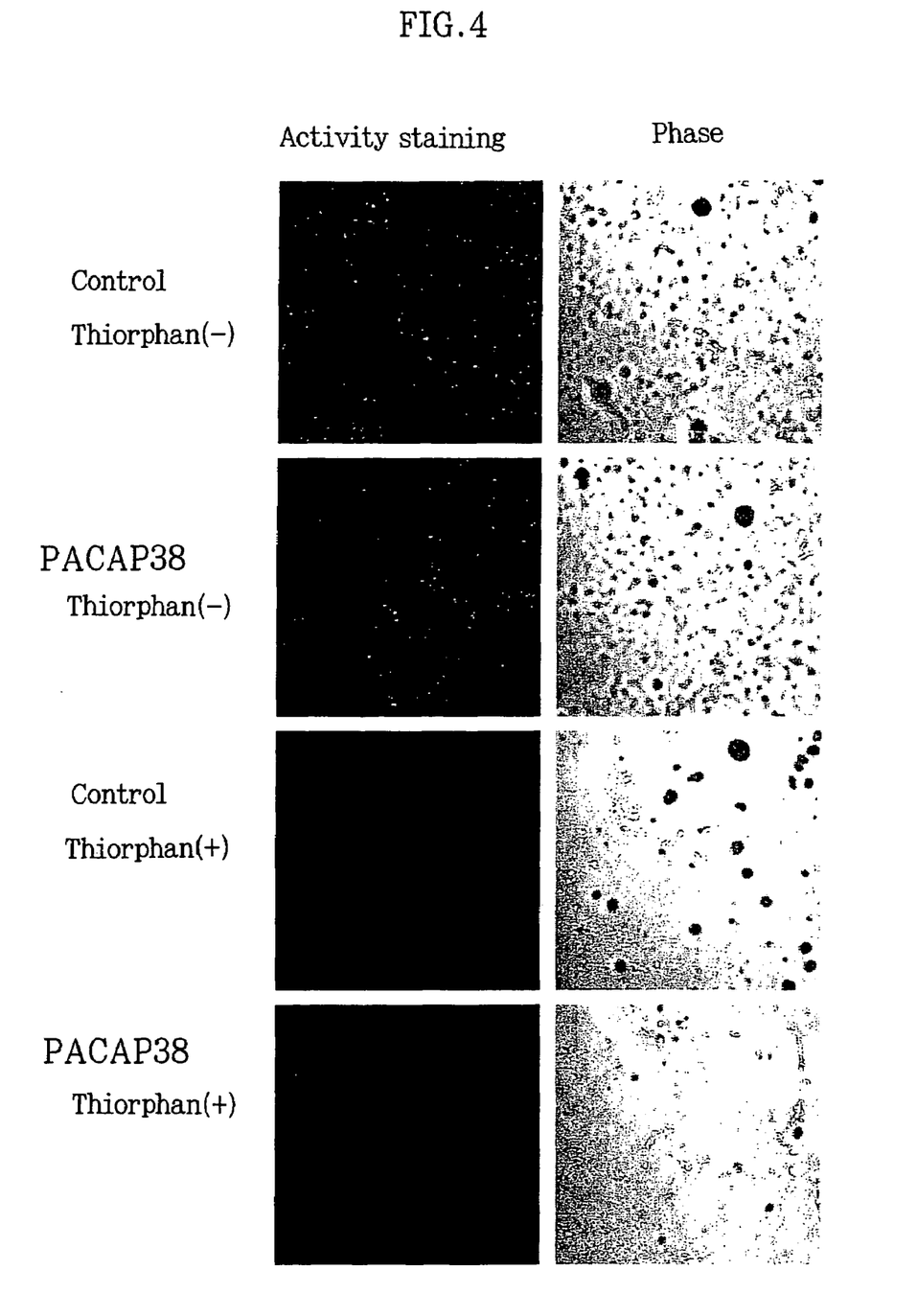
FIG. 4 is a microscopic photograph showing the effects of PACAP and thiorphan against the neprilysin activity in mouse primary cultured nerve cells.

PACAP (PACAP 38, final concentration: 1 µM) was added and treated as in EXAMPLE 2. The results are shown in FIG. 4. By the addition of PACAP, the neprilysin activity of the nerve cells markedly decreased when compared to control added with no PACAP. Also, it was confirmed that this neprilysin enzyme activity was specific to neprilysin, since the neprilysin enzyme activity almost completely disappeared by adding a neprilysin-specific enzyme inhibitor or thiorphan (Sigma T6031, final concentration: 10 µM) to the substrate solution.

INDUSTRIAL APPLICABILITY

The compounds enhancing the activity and/or expression of neprilysin, which are obtained by the screening method characterized by using the method of measuring the activity of neprilysin according to the present invention, are useful as agents for promoting Aβ degradation or removing Aβ and furthermore as preventive and/or therapeutic agents for Alzheimer's disease, utilizing the neprilysin activity. Also, the activity measuring method of the present invention can be used for presymptomatic diagnosis of Alzheimer's disease.

The invention claimed is:

1. A method for selecting a compound that enhances the activity of neprilysin which comprises:
   incubating an isolated nerve cell comprising neprilysin with a test compound, a substrate of neprilysin, aminopeptidase, phosphoramidon, and nitrosalicylaldehyde to form a fluorescent substance; and
   measuring an increase in fluorescence in said cell relative to a control cell, wherein the increase in fluorescence identifies a test compound that enhances neprilysin activity.

2. The method according to claim 1, wherein the nerve cell is fixed.

3. The method according to claim 1, wherein the nerve cell is fixed with paraformaldehyde.

4. The method according to claim 1, wherein the nerve cell is a cultured cell.

5. The method according to claim 4, wherein the nerve cell is present in a primary culture.

6. The method according to claim 1, wherein the nerve cell comprises a dendrite.

7. The method according to claim 1, wherein the nerve cell comprises an axon.

8. The method according to claim 1, wherein the nerve cell comprises a synaptic terminal.

9. The method according to claim 1, wherein the nerve cell comprises a synaptic vesicle.

10. The method according to claim 1, wherein the nerve cell is from the cerebral cortex or the hippocampus.

11. The method according to claim 1, wherein 4-methoxy-2-naphthylamide is produced by neprilysin-dependent degradation of a substrate of neprilysin.

12. The method according to claim 11, wherein the fluorescent substance is produced from a reaction of 4-methoxy-2-naphthylamide and nitrosalicylaldehyde.

13. The method according to claim 11, wherein the substrate is glutaryl-alanyl-alanyl-phenylalanyl-4-methoxy-2-naphthylamide.

14. The method according to claim 1, wherein 4-methoxy-2-naphthylamide is produced by treating the substrate of neprilysin glutaryl-alanyl-alanyl-phenylalanyl-4-methoxy-2-naphthylamide with neprilysin and an aminopeptidase.

15. The method according to claim 1, wherein 7-amino-4-methylcoumarin is produced by treating the substrate of neprilysin succinyl-alanyl-alanyl-phenylalanyl 4-methylcoumarin-7-amide with neprilysin.

16. The method according to claim 1, wherein the fluorescent substance is 7-amino-4-methylcoumarin.

17. The method of claim 1, wherein the compound enhances neprilysin activity by about 10%.

18. A method for screening a compound that enhances the activity of neprilysin in a nerve cell, which comprises:
   incubating an isolated nerve cell with or without a test compound,
   fixing the nerve cell with a fixing agent,
   reacting a substrate of neprilysin with the nerve cell to form a reaction mixture,
   adding aminopeptidase, phosphoramidon, and nitrosalicylaldehyde to the reaction mixture,
   obtaining a positively stained image of the nerve cell by a confocal laser scanning microscope,
   measuring neprilysin activity for both the nerve cells incubated wit the test compound and without the test compound based on the stained image,
   comparing the neprilysin activity between the nerve cells incubated with the test compound and without the test compound, and
   selecting a compound that enhances the neprilysin activity by about 10% or more.

* * * * *

SEQUENCE LISTING

<160> NUMBER OF SEQ ID NOS: 2

<210> SEQ ID NO 1
<211> LENGTH: 14
<212> TYPE: PRT
<213> ORGANISM: Unknown Organism
<220> FEATURE:
<223> OTHER INFORMATION: Description of Unknown Organism: Somatostatin
      peptide

<400> SEQUENCE: 1

Ala Gly Cys Lys Asn Phe Phe Trp Lys Thr Phe Thr Ser Cys
 1               5                  10

<210> SEQ ID NO 2
<211> LENGTH: 11
<212> TYPE: PRT
<213> ORGANISM: Unknown Organism
<220> FEATURE:
<223> OTHER INFORMATION: Description of Unknown Organism: Substance P
      peptide

<400> SEQUENCE: 2

Arg Pro Lys Pro Gln Gln Phe Phe Gly Leu Met
 1               5                  10